United States Patent
Eklund et al.

(10) Patent No.: US 9,295,796 B2
(45) Date of Patent: Mar. 29, 2016

(54) BREATHING SYSTEM WITH FLOW ESTIMATION

(75) Inventors: Mathias Eklund, Stockholm (SE); Fredrik Norrby, Upssala (SE); Magnus Hallbäck, Danderyd (SE)

(73) Assignee: Maquet Critical Care AB, Solna (SE)

(*) Notice: Subject to any disclaimer, the term of this patent is extended or adjusted under 35 U.S.C. 154(b) by 558 days.

(21) Appl. No.: 13/699,072

(22) PCT Filed: May 22, 2010

(86) PCT No.: PCT/EP2010/057083
§ 371 (c)(1),
(2), (4) Date: Mar. 26, 2013

(87) PCT Pub. No.: WO2011/147438
PCT Pub. Date: Dec. 1, 2011

(65) Prior Publication Data
US 2013/0192600 A1   Aug. 1, 2013

(51) Int. Cl.
*A61M 16/00* (2006.01)
*A61M 16/04* (2006.01)
(Continued)

(52) U.S. Cl.
CPC ....... *A61M 16/0057* (2013.01); *A61M 16/0051* (2013.01); *A61M 16/04* (2013.01); *A61M 16/06* (2013.01); *A61M 16/0816* (2013.01); *A61M 16/0875* (2013.01); *A61M 2016/0021* (2013.01); *A61M 2016/0036* (2013.01); *A61M 2205/3331* (2013.01); *A61M 2205/3334* (2013.01); *A61M 2205/3344* (2013.01); *A61M 2230/46* (2013.01)

(58) Field of Classification Search
None
See application file for complete search history.

(56) References Cited

U.S. PATENT DOCUMENTS

| 5,551,419 A | 9/1996 | Froehlich et al. |
| 5,769,608 A * | 6/1998 | Seale ............... F04B 43/04 417/360 |

(Continued)

FOREIGN PATENT DOCUMENTS

| EP | 0722747 A2 | 7/1996 |
| EP | 1421902 A1 | 5/2004 |

(Continued)

OTHER PUBLICATIONS

International Preliminary Report on Patentability, issued Nov. 27, 2012, for International Patent Application No. PCT/EP2010/057083 having an international filing date of May 22, 2010.

(Continued)

*Primary Examiner* — Tan-Uyen (Jackie) T Ho
*Assistant Examiner* — Joseph D Boecker
(74) *Attorney, Agent, or Firm* — Schiff Hardin LLP (57) ABSTRACT

A breathing system for ventilating a patient has a gas channel enclosing a gas channel volume (V), and a compliance (C). The system has a flow calculation unit operative to determine a gas flow estimate (Fe) at a flow estimate location in the gas channel. The gas flow estimate (Fe) is based on a relationship between a monitored gas flow (Fm) in the gas channel and a compressible gas flow (Fc) which depends on the compliance (C) in the gas channel. The monitored gas flow (Fm) is a gas flow at a monitoring location in the gas channel and the compressible gas flow (Fc) is a flow of gas in the gas channel between the flow estimate location and the monitoring location, and the flow estimate location is remote from the monitoring location.

23 Claims, 6 Drawing Sheets (51) Int. Cl.
*A61M 16/06* (2006.01)
*A61M 16/08* (2006.01)

(56) References Cited

U.S. PATENT DOCUMENTS

| | | | | |
|---|---|---|---|---|
| 5,865,168 | A * | 2/1999 | Isaza | A61M 16/00 128/200.24 |
| 6,017,315 | A | 1/2000 | Starr et al. | |
| 6,105,575 | A * | 8/2000 | Estes | A61M 16/00 128/204.21 |
| 6,155,986 | A * | 12/2000 | Brydon | A61B 5/087 128/911 |
| 6,342,040 | B1 | 1/2002 | Starr et al. | |
| 6,557,553 | B1 | 5/2003 | Borrello | |
| 6,644,312 | B2 * | 11/2003 | Berthon-Jones | A61M 16/00 128/204.18 |
| 6,688,307 | B2 * | 2/2004 | Berthon-Jones | A61M 5/085 128/204.21 |
| 7,168,429 | B2 * | 1/2007 | Matthews | A61M 16/0051 128/204.21 |
| 8,136,521 | B2 * | 3/2012 | Matthews | A61M 16/0051 128/200.24 |
| 8,474,455 | B2 * | 7/2013 | Soliman | A61M 16/0051 128/200.24 |
| 8,881,727 | B2 * | 11/2014 | Aloia | A61B 5/087 128/204.18 |
| 2002/0023644 | A1 * | 2/2002 | Berthon-Jones | A61B 5/085 128/204.22 |
| 2004/0097821 | A1 | 5/2004 | Blomberg et al. | |
| 2007/0255161 | A1 | 11/2007 | De Backer | |
| 2009/0241955 | A1 * | 10/2009 | Jafari | A61M 16/0051 128/204.23 |
| 2011/0146681 | A1 * | 6/2011 | Jafari | A61B 5/085 128/204.21 |
| 2013/0284173 | A1 * | 10/2013 | Masic | A61B 5/08 128/204.33 |

FOREIGN PATENT DOCUMENTS

| | | | |
|---|---|---|---|
| WO | 99/43388 | A1 | 9/1999 |
| WO | 02/20076 | A2 | 3/2002 |
| WO | 2006/037627 | A2 | 4/2006 |
| WO | WO 2008028247 | A1 * | 3/2008 ............ A61M 16/06 |

OTHER PUBLICATIONS

International Search Report, mailed Feb. 10, 2011, for International Patent Application No. PCT/EP2010/057083 having an international filing date of May 22, 2010.

* cited by examiner

BREATHING SYSTEM WITH FLOW ESTIMATION

BACKGROUND OF THE INVENTION

1. Field of the Invention

This invention pertains in general to the field of breathing systems for providing a flow of gas to a patient.

More precisely, the invention relates to determining the actual flow in such breathing systems for safety purposes.

2. Description of the Prior Art

Various breathing systems for regulating a flow of gas to a patient are known. Such breathing systems include for instance anesthesia machines, intensive care ventilators with added anesthesia capabilities, etc.

Conventional breathing systems have a flow meter at a location where it is desired to measure the gas flow. However, this adds a dead volume and may increase the flow resistance in the breathing system. Further problems with flow meters at the y-piece include difficulties in handling moisture and mucus from the patient, quick temperature changes between expiratory and inspiratory gas, and varying gas compositions, e.g. of $CO_2$ and anesthetic agent. An alternative is to estimate a flow based on measurements at a location different from the location where it is desired to measure the gas flow.

An erroneous estimation of flow in breathing devices may involve a safety hazard potentially exposing a connected patient to situations with dire consequences, e.g. when a non-desired amount of a substance is delivered to the patient.

A source for incorrect estimation and regulation of the gas flow is the compressible internal volume of the breathing system which affects the actual gas flow, for example at a patient connection. As mentioned above, prior art apparatus often use several flow meters at critical locations in the breathing system to measure the flow.

For instance, US 2007/0089738 discloses a system for circuit compliance compensated volume control in a patient respiratory ventilation system. It is disclosed a flow regulated feedback control loop, where the patient volume is estimated. A flow meter is installed at the y-piece of the patient connection to measure the patient flow. The patient flow is used to compute a measured patient volume and the flow is continuously monitored.

EP 0723785 discloses a ventilator system comprising a connection system for connecting to a patient. A transfer function of the connection system is determined by a well known automatic control model to compensate for the influence of the connection system on the flow of gas supplied to the patient. In order to determine the transfer function several gas flows must be measured. Either a test lung is connected to the connection system, having pressure and flow meters, or the transfer function is determined without the test lung by using inspiratory flow and pressure as input signals, and expiratory flow and pressure as output signals to the automatic control model.

Having an increased number of measuring points in the breathing system do still not compensate for the actual compressive volume effect. Also, flow meters are expensive and have inherent drawbacks depending on measuring technique. There is a need for a simpler system, where the actual flow can be determined without flow meters, or where flow meters are not possible to use.

Thus, there is a need to provide alternatives or improvements avoiding the aforementioned issues. It would for instance be advantageous to be able to estimate the actual gas flow at a desired location in the breathing system taking into account the compressive volume in the breathing system. The compressive volume is particularly critical when small children and infants are connected to the breathing system, whose lung volume is comparatively small in relation to the volume of the breathing system.

It would be further advantageous to estimate the flow without the use of flow meters.

Hence, an improved or alternative breathing system allowing for determining the actual gas flow at a location such as a patient connection in a breathing system would be advantageous. This allows in particular for increased cost-effectiveness, improved reliability, versatility, and/or patients safety.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a breathing system, a method, and a computer program according to the appended patent claims.

According to a first aspect of the invention, a breathing system for ventilating a patient is provided. The breathing system has a gas channel enclosing a gas channel volume (V), and a compliance (C). The system has a flow calculation unit operative to determine a gas flow estimate (Fe) at a flow estimate location in the gas channel. The gas flow estimate is based on a relationship between a monitored gas flow (Fm) in the gas channel and a compressible gas flow (Fc) which depends on the compliance (C) in the gas channel. The monitored gas flow is a gas flow at a monitoring location in the gas channel and the compressible gas flow (Fc) is a flow of gas in the gas channel between the flow estimate location and the monitoring location. The flow estimate location is remote from the monitoring location.

According to a second aspect of the invention, a method is provided for internally operating a breathing system that gas channel enclosing a gas channel volume (V). The system has a compliance (C). The method includes determining a gas flow estimate (Fe) at a flow estimate location in the gas channel. The gas flow estimate is based on a relationship between a monitored gas flow (Fm) in the gas channel and a compressible gas flow (Fc) which depends on the compliance in the gas channel. The monitored gas flow is determined at a monitoring location in the gas channel and the compressible gas flow (Fc) is a flow of gas in the gas channel between the flow estimate location and the monitoring location. The flow estimate location is remote from the monitoring location.

According to a third aspect of the invention a non-transitory, computer-readable data storage medium encoded with programming instructions is provided, for processing by a computer. The programming instructions include code segments for measuring at least one pressure at a pressure measurement location in a breathing system having a compliance, determining an estimated pressure (Pe) in the breathing system from the at least one pressure, determining a compressible gas flow (Fc) in the breathing system based on a relationship between the compliance and a differential of the estimated pressure, determining a gas flow estimate (Fe) in the breathing system based on a relationship between the compressible gas flow and a monitored gas flow (Fm) in the breathing system. The gas flow estimate is determined at a flow estimate location, and the monitored gas flow is determined at a monitoring location in the gas channel. The flow estimate location is remote from the monitoring location, and/or the flow estimate location is remote from the at least one pressure measurement location.

Some embodiments provide for determining the actual gas flow at various locations in the breathing system. This has several advantages. There is a need of having an accurate control of the inspiratory and expiratory breathing cycles. Determining the correct flow for example at a patient interface, such as a patient tube or mask would advantageously allow correct control of such breathing cycles. For instance, it is desirable to detect when the expiratory flow from the patient is zero for controlling a correct frequency of the breathing cycle. Another example is in pressure support control, when a gas flow threshold is defined for triggering the next cycle. Determining the actual patient gas flow allows a correct threshold to be defined.

Some embodiments provide for determining the actual volume delivered to the patient, for example to detect losses, and not only the gas delivered by the gas sources.

DESCRIPTION OF THE PREFERRED EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to an anesthesia machine and in particular to an anesthesia machine having a circle system. However, it will be appreciated that the invention is not limited to this application but may be applied to many other breathing apparatuses, including for example intensive care ventilators, with or without added anesthesia capabilities etc.

Figure 1:
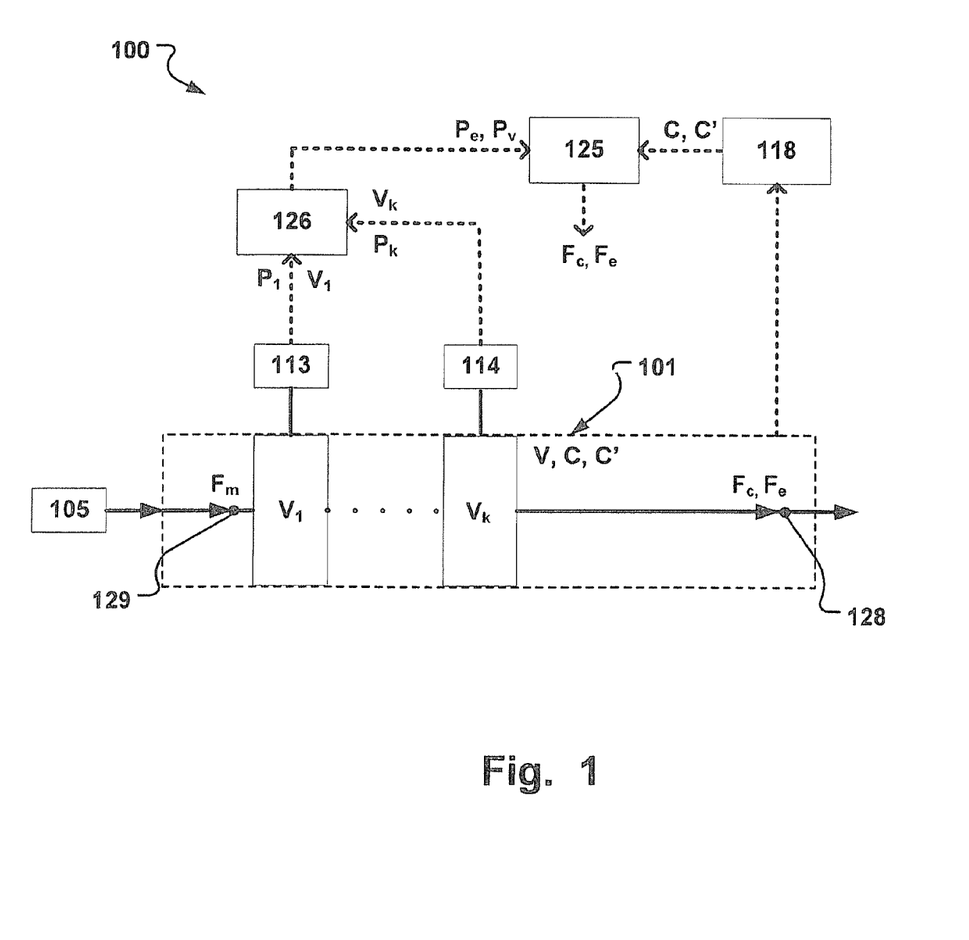
FIG. 1 is a schematic illustration of a breathing system according to an embodiment.

FIG. 1 shows a schematic illustration of breathing system 100 according to an embodiment of the invention. The breathing system 100 may be used for ventilating a patient.

The system 100 has a gas channel 101, which has a gas channel volume (V), which may be the total internal volume of the gas channels 101 of the system and any devices connected for gas interaction in the system, denoted as volumes $V1, \ldots Vk$, which is a plurality of sub volumes of the gas channel volume (V). A gas channel 101 is to be interpreted as a gas conduit.

The breathing system 100, and also the breathing systems 200, 500, discussed further below, have a compliance (C) defined as $C=dVc/dP$, where $dVc$ is the compressed gas volume in the breathing system 100 between the flow estimate location 128 and the flow monitoring location 129, when the pressure in the system undergoes a pressure change $dP$.

The system has a flow calculation unit 125 operative to determine a gas flow estimate (Fe) at a flow estimate location 128 in the gas channel 101. The gas flow estimate (Fe) is based on a relationship between a monitored gas flow (Fm) in the gas channel 101 and a compressible gas flow (Fc) which depends on the compliance (C) in the gas channel 101. The compressible gas flow (Fc) is a change of the compressed gas volume (Vc) over a time interval (dt), $Fc=dVc/dt$. The monitored gas flow (Fm) may be a gas flow at a monitoring location 129 in the gas channel 101 and the compressible gas flow (Fc) may be a flow of gas in the gas channel between the flow estimate location 128 and the monitoring location 129. The flow estimate location 128 may be remote from the monitoring location 129. The gas flow estimate (Fe) may thus be determined anywhere in the breathing system 100, for example remote from the flow monitoring location 129. The gas flow estimate (Fe) may accordingly be determined at the flow estimate location 128 in the breathing system 100 without the presence of a flow sensor at the location 128. Determining the gas flow estimate (Fe) may be construed as calculating the gas flow (Fe).

The system 100 may have at least one pressure sensor 113, 114, in communication with the system 100 for measuring at least one pressure $P1, Pk$, at a pressure measurement location in the system 100 respectively. It is not necessary for the pressure sensors 113, 114, to be positioned at the respective pressure measurement location. However, the location of the respective pressure sensor is to be construed as the location of the respective pressure measurement location for the remainder of the disclosure.

The system 100 has a pressure estimator unit 126 connected to the pressure sensor 113, 114. The pressure estimator unit 126 is operative to determine an estimated pressure (Pe) in the system 100 based on the at least one pressure $P1, Pk$, measured by the pressure sensors 113, 114. The estimated pressure (Pe) is a good estimation of the pressure in the volume $(V1, \ldots, Vk)$ between the flow estimate location 128 and the flow monitoring location 129.

The flow calculation unit 125 is operative to determine the compressible gas flow (Fc) based on a relationship between the compliance (C) and a differential of the estimated pressure (Pe) for providing the gas flow estimate (Fe) anywhere in the system 100, for example remote from any pressure measurement location. The estimated pressure (Pe) may be a function of time (t).

The system 100 has a gas source 105, or a multiple of gas sources (not shown), in communication with the system 100. The monitored gas flow (Fm) may be a measured flow anywhere in the system 100 at a monitoring location 129, or a known flow from the gas source 105 into the system 100, i.e. a generated flow.

The system 100 has a compliance estimator unit 118 which is operative to determine the compliance (C) in the system 100. The compliance may be a location specific compliance (C') at an arbitrary location in the gas channel 101, such as between the flow estimate location 128 and the monitoring location 129. The flow calculation unit 125 may accordingly determine the compressible gas flow (Fc) between the flow estimate location 128 and the monitoring location 129 based on the compliance (C'), and subsequently determine the gas flow estimate (Fe) at the flow estimate location 128 by compensating the monitored gas flow (Fm) with the compressible gas flow (Fc).

The flow calculation unit 125 may be operative to determine the compressible gas flow (Fc) according to the relationship Fc=C*dPe/dt, where C is the compliance of the system 100, which may also may be the location specific C', and where the differential of the estimated pressure is dPe/dt which is the time derivative of the estimated pressure (Pe). The estimated gas flow (Fe) may be expressed as Fe=Fm−Fc, and accordingly as Fe=Fm−C*dPe/dt.

The compressible gas flow (Fc) may be the gas flow required to build up the pressure in the system 100 during a time interval (dt) due to the compressible gas volume (dVc) of the system 100, where the compressible gas flow (Fc) can be described as Fc=dVc/dt=C*dPe/dt, as a gas flow may be expressed as F=V/t, where V is the volume and t the time.

Figure 2:
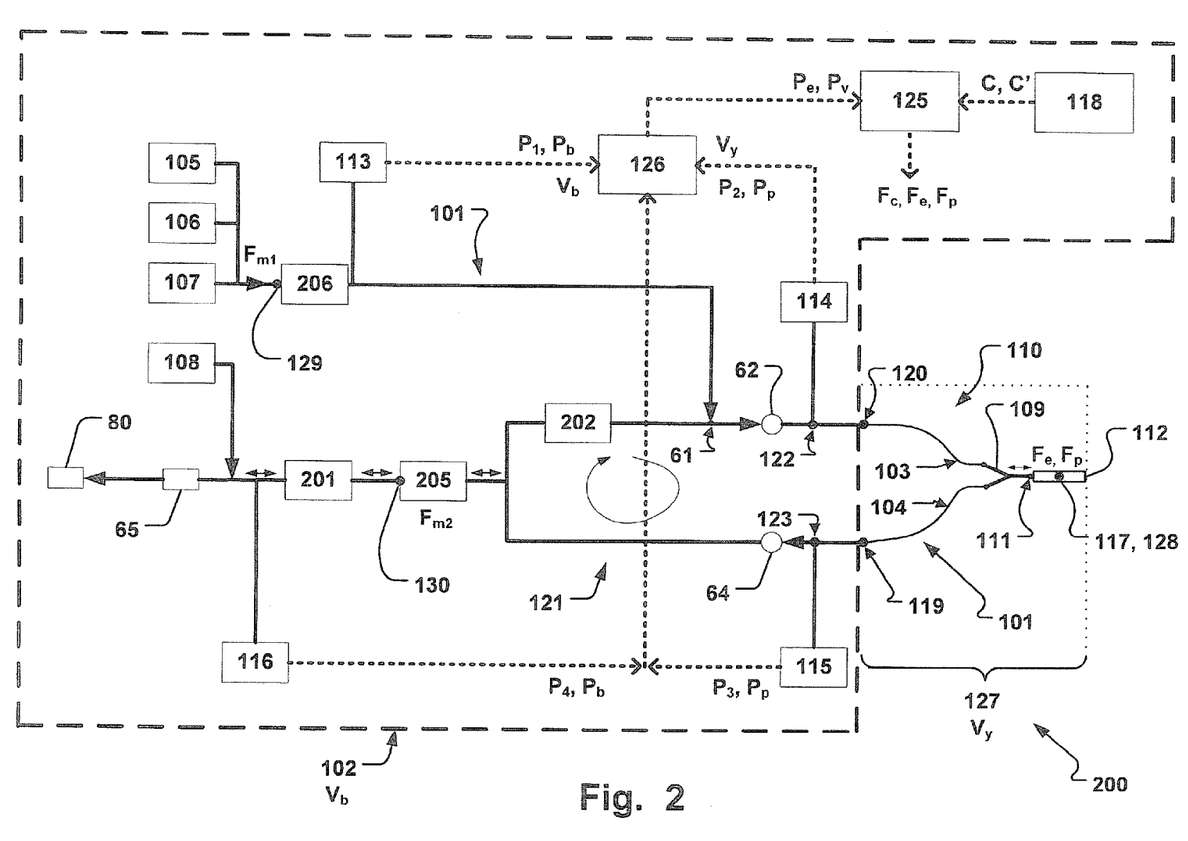
FIG. 2 is a schematic illustration of a breathing system according to an embodiment.

FIG. 2 shows a schematic illustration of breathing system 200 according to an embodiment of the invention. The breathing system 200 may be used for ventilating a patient.

Fresh gas to be entered into a circle system 121 is delivered by controllable fresh gas sources, such as a first gas source for air 105, a second gas source 106 for oxygen, and a third gas source for nitrous oxide 107. A desired mixture of these gases may be chosen by a user of the system 200 or automatically adjusted in dependence of user settings and other conditions in the breathing system 200, in a known manner.

Gasified anesthetic agents enters the circle system 121 in a fresh gas mixture at entry point 61. The anesthetic agents are gasified by one or more vaporizers (not shown). The vaporizers may be anesthetic delivery devices as known in the art, including one of an injection vaporizer, or an evaporation vaporizer, for adding the volatile liquid anesthetic agent in gasified form to the fresh gas flow. The vaporized anesthetic agent adds an extra gas flow to the fresh gas flow.

Inspiratory check valve 62 and expiratory check valve 64 ensure the flow direction in the circle system 121. Expiratory valve 65 is closed during inspiration and controls a release from the circle system 121, e.g. to an evacuation system 80 or similar during expiration. A volume reflector 201 may be present in the breathing circuit 102. The volume reflector 201 may ensure refilling of the circle system with e.g. previously exhaled gas during inspiration, as provided by a controllable gas source 108, usually of an oxygen gas source. A ratio of rebreathing is suitable adjusted by a control unit of the breathing system (not shown). The ratio of rebreathing is adjusted by suitably controlling fresh gas sources 105-107 and gas source 108 for the reflector during inspiration. A flow meter 205 may be present in the breathing circuit 102, which may function as an expiratory flow meter during expiration or as a flow meter for redundant flow measurements during inspiration.

The system 200 includes the breathing circuit 102 and patient tubing 127 connected to the breathing circuit 102. The system 200 has a gas channel volume (V), which may be the total internal volume of the gas channels 101 of the system 200 and any devices connected for gas interaction in the system such as a reflector 201 and a $CO_2$ absorber 202, and including the internal volume of any patient tubing 127.

As mentioned above the compliance (C) for the system 200 may be defined as C=dVc/dP, where dVc is the compressed gas volume in the system 200 when the pressure in the system undergoes a pressure change dP, where the pressure (P) may correspond to the estimated pressure (Pe).

Pressure sensors 113, 114, 115, and 116 are in communication with the breathing circuit 102 for measuring at least one pressure (P1, P2, P3, P4) at a pressure measurement location in the breathing circuit 102 respectively.

The system 200 includes gas sources 105, 106, 107, and 108 in communication with the breathing circuit 102.

The pressure estimator unit 126 is connected to the pressure sensors 113-116 and is operative to determine an estimated pressure (Pe) in the system 200 based on the at least one pressure (P1, P2, P3, P4) measured by the at least one pressure sensors 113-116. The total gas flow output or monitored gas flow (Fm) from the at least one gas source 105-108 may be determined by a flow meter 206 (Fm1) at a monitoring location 129 adjacent to the at least one gas source 105-108, and/or by flow meter 205 (Fm2) at a monitoring location 130. The total monitored flow may be described as Fm=Fm1+Fm2.

The gas flow estimate (Fe) may be determined anywhere in the breathing system 200, remote from monitoring locations 129, 130. The gas flow estimate (Fe) may accordingly be determined at the flow estimate location 117, 128 in the breathing system 200 without the presence of a flow sensor at the location 117, 128.

The gas flow estimate (Fe) may be a patient gas flow (Fp) in the patient tubing 127. The patient gas flow (Fp) may then be determined according to the relationship Fp=Fm−C*dPe/dt.

The compressible gas flow (Fc) required to build up the pressure in the system 200 during a time interval (dt) due to the compressible gas volume (dVc) of the system 100 may be different during inspiration and expiration, for instance as the estimated pressure (Pe) may be different, as described further below.

The patient tubing 127 has y-piece tubing 110 which comprises an inspiratory tube 103 and an expiratory tube 104, and a y-piece 109 connectable to the breathing circuit 102 via y-piece tubing 110. The y-piece 109 has a patient connection port 111. The patient tubing 127 comprises further a patient interface 112 connected to the patient connection port 111.

The flow estimate location (Fe) may correspond to a patient interface location 117 in the patient interface 112, and the patient gas flow (Fp) may accordingly be determined at the patient interface location 117.

The patient interface 112 may include a tracheal tube or patient mask. The volume of the y-piece tubing 110, y-piece 109 and patient interface 112 are below referred to as patient tubing volume (Vy).

The volume of the breathing circuit 102 may be well defined. In that case the unknown part of the gas channel volume (V) is the patient tubing volume (Vy). Vy varies depending on the dimensions of the inspiratory tube 103, expiratory tube 104, y-piece 109, and patient interface 112. Hence, as the compressed gas volume (dVc) during a change in pressure dPe depends on the gas channel volume (V) and thereby the patient tubing volume (Vy), the compliance (C) of the system 200 is affected by the patient tubing volume (Vy).

Returning to the patient flow Fp=Fm−C*dPe/dt, Fm may be the total gas flow output from the at least one gas source 105-108 into the breathing circuit 102. The actual gas flow at the patient connection may accordingly be determined. During inspiration C*dPe/dt is subtracted from the monitored gas flow (Fm). During expiration the gas flow detected, e.g. by expiratory flow meter 205 at monitoring location 130, may be corrected by adding C*dPe/dt to compensate the compressible gas volume (dVc).

The estimated gas flow (Fe), which accordingly is a measure of the actual gas flow, may be determined at any location in the breathing system 200 according to the relationship Fe=Fm±C'*dPe/dt, where Fm is the monitored gas flow measured by flow meter 206 at the gas sources during inspiration or the gas flow measured by the expiratory flow meter 205 during expiration, or another monitored flow at an arbitrary location in the system 200, and where C'*dPe/dt is the flow required to build up sufficient pressure at the flow estimate location due to the compressive volume, and C' is the compliance between the flow estimate location and the monitoring location.

A certain amount of gas is required to build up sufficient pressure in the channels 101, absorber 202, reflector 201, patient tubing 127 etc during a time interval (dt), therefore the total gas flow input has to be corrected with the gas flow required for this pressure buildup.

If the actual gas flow, which corresponds to the estimated gas flow (Fe) is to be determined at a location in the breathing circuit 200 corresponding to the location of the at least one pressure sensor 113-116, the estimated pressure (Pe) may be the pressure measured by the at least one pressure sensor 113-116. The estimated pressure (Pe) may be a mean pressure representing a close estimate of the pressure in the compressed gas volume at the flow estimate location 117, 128, remote from pressure sensors 113-116, or the pressure between the gas sources, or any flow meter, and the flow estimate location 117, 128. The estimated pressure (Pe) may be a volume weighted pressure (Pv) as described below.

The at least one pressure measurement location may be positioned away from the patient interface location 117 by at least a distance corresponding to the length of the y-piece tubing 110. In FIG. 2 the gas sensors 114 and 115 have pressure measurement locations 122 and 123, respectively. The patient interface location 117, at which the patient flow (Fp) is determined, is remotely separated from the pressure measurement locations 122, 123, by at least a distance corresponding to the length of the inspiratory tube 103, or expiratory tube 104. The presence of flow meters at the y-piece tubing 110, y-piece 109, and patient interface 112 is not required. This is due to utilization of the pressure measurements in the breathing circuit 102 for determining an estimated pressure (Pe) by the pressure estimator unit 126, and the flow calculation unit 125 for determining the gas flow estimate (Fe) based on the aforementioned relationship between the time derivative of the estimated pressure (Pe) and the compliance (C, C') of the system 200.

The estimated pressure (Pe) may be a volume weighted pressure (Pv) with respect to the gas channel volume (V). A volume weighted pressure in the breathing systems 100, 200, or breathing system 500 described further below, is used instead of a single pressure, in order to handle pressure differences between different parts of the system 100, 200, 500, due to internal flow resistances. Thereby the effect of the different volumes in the system 100, 200, 500, is accounted for in order to provide an accurate pressure estimation. Due to different pressures in the system 100, 200, 500, the gas flow required to build up a sufficient pressure in the system 100, 200, 500, to compensate for compressive gas volumes would have to be determined for all different parts of the system 100, 200, 500. This has the same effect as determining a volume weighted pressure (Pv) for the system 100, 200, 500. A pressure sensor in a large volume is weighted heavier than a pressure sensor in a small volume.

The patient gas flow (Fp) may thus be determined accurately by the flow calculation unit 125 based on the time derivative of the volume weighted pressure (Pv), Fp=Fm−C*dPv/dt.

As illustrated in FIG. 1, the gas channel volume (V) may have a number of sub volumes (Vk). The pressure estimator unit 126 may be operative to determine the volume weighted pressure (Pv) according to the relationship Pv=Σ(Vk*Pk)/ΣVk, where Pk is the measured pressure in each of the plurality of sub volumes respectively.

A number of definitions are hereby introduced to exemplify the estimation of the volume weighted pressure (Pv).

With reference to FIG. 2, the multiple sub volumes may comprise a breathing circuit volume (Vb) of the aforementioned breathing circuit 102 and a patient tubing volume (Vy) of the aforementioned patient tubing 127.

The at least one pressure sensor may comprise at least one breathing circuit pressure sensor 113, 116, adjacent to the breathing circuit volume (Vb) for providing a breathing circuit pressure (Pb). The at least one pressure sensor further has at least one patient tubing pressure sensor 114, 115, for providing a patient tubing pressure (Pp). The pressure estimator unit may be operative to determine the volume weighted pressure (Pv) according to the relationship Pv=(Vb*Pb+Vy*Pp)/(Vb+Vy).

The y-piece tubing 127 may be connected to the breathing circuit 102 at expiration and inspiration ports 119, 120, of the system 200. At least one patient tubing pressure sensor 114, 115, is adjacent to at least one of the expiration and inspiration ports 119, 120. The most accurate pressure of the respective volumes is provided by measurement by pressure sensors adjacent to each of the respective volumes. Adjacent is to be construed as the pressure measurement location being sufficiently close to the respective volumes to provide an accurate measure of the pressure in the respective volumes.

The compliance estimator unit 118 may be operative to determine the compliance (C) of the system 200 based on a breathing circuit compliance (Cb) and a y-piece compliance (Cy) when the patient connection port 111 is plugged. Thus, the compliance (C) may comprise the breathing circuit compliance (Cb) and a y-piece compliance (Cy). The y-piece compliance (Cy) is the compliance of the y-piece tubing 110, the y-piece 109, and the patient interface 112. The patient tubing volume (Vy) may be determined according to the relationship Vy=Cy*Patm, where Patm is the absolute pressure. Vb may be determined from the design of the breathing circuit 102. Hence, the volume of the breathing circuit (Vb) and the compliance of the breathing circuit (Cb) may be known. In order to determine the total compliance of the system 200, taking into account the compressive volume of the y-piece tubing 110 and y-piece 109, the compliance estimator unit 118 may initially calculate the system compliance (C) with the y-piece port 111 sealed. A patient flow (Fp) may then be determined at the unplugged y-piece port 111 according to aforementioned relationship between the compliance (C) and the estimated pressure (Pe). If the gas channel volume (V) of the breathing system 200 is changed a new compliance (C) may be determined.

The patient interface 112 may have a proximal part at the patient connection port 111 and an opposite distal part. The distal part may be the part of the patient interface 112 arranged for insertion into a patient, such as the end of a tracheal tube. The patient gas flow (Fp) may be determined at the distal part. Accordingly, the compliance estimator unit 118 may be operative to determine the compliance (C) of the system 200 based on aforementioned breathing circuit compliance (Cb) and the y-piece compliance (Cy) when the distal part of the patient interface 112 is plugged. In this case the y-piece compliance (Cy) is the compliance of the y-piece tubing 110, the y-piece 109, and the patient interface 112. The patient interface 112 may have a patient tube, such as a tracheal tube, or a mask to be placed over the patient. A number of different patient interfaces 112 having different geometrical dimensions may be connected to the patient connection port 111. By determining the y-piece compliance (Cy) for each of the patient interfaces 112, the flow at the distal part of each patient interface 112 may be determined. Thus, when the tracheal tube is inserted in the patient, a flow in the upper airways is estimated.

The y-piece compliance (Cy) may be manually entered depending on the type of y-piece 109, patient interface 112, inspiratory tube 103, or expiratory tube 104.

In FIG. 2, the at least one gas source comprises a fresh gas source 105, 106, 107, and a drive gas source 108. Two breathing circuit pressure sensors 113, 116, are adjacent to each of the fresh gas sources and the drive gas source. Two patient tubing pressure sensors 114, 115, are adjacent to each of the expiration and inspiration ports 119, 120. By having the pressure sensors at the end points of the system 200 an optimal estimation of pressure is provided, as there is no gas flow and thereby pressure drop that is not occurring between two pressure sensors. The pressure sensors 114, 115, are thereby utilized for determining an accurate volume weighted pressure (Pv) and subsequently the actual patient flow (Fp), and not only used for measuring the pressure at the y-piece 109. If the internal flow resistances are known for the different parts of the system 200 the pressure may be estimated for the different parts of the system 200, fewer pressure sensors may be used. Having pressure sensors in the breathing circuit 102 close to the expiration and inspiration ports 119, 120, may provide a quicker response for the patient gas flow (Fp).

Further definitions are hereby introduced to exemplify an estimation of the volume weighted pressure (Pv) for the system 200.

Figure 3:
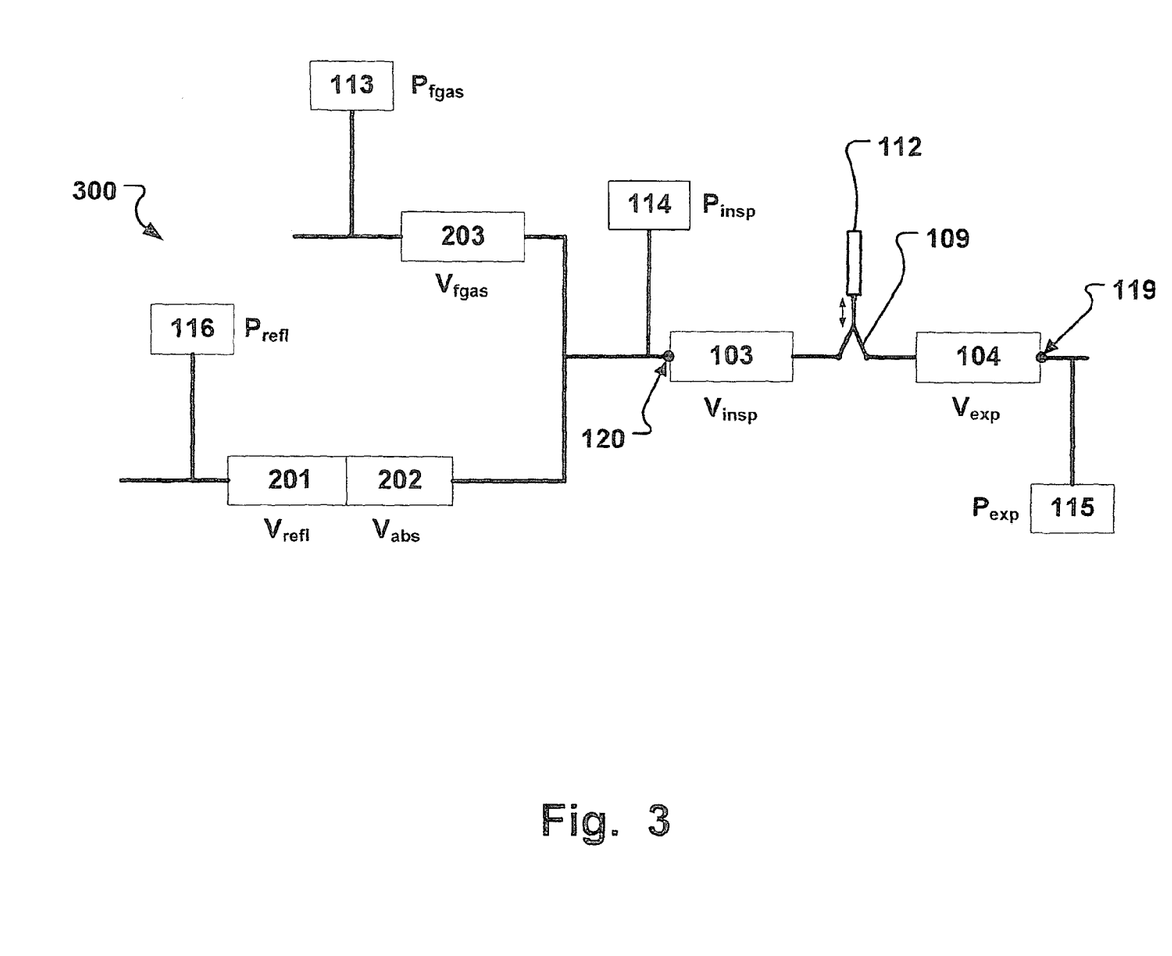
FIG. 3 is a schematic illustration of a breathing system for determining a volume weighted pressure according to an embodiment.

FIG. 3 shows schematic details of a breathing system 300 which is a simplified overview for illustrating the gas channel volumes (V) of the system 200 in FIG. 2 during the inspiratory phase. The breathing circuit volume (Vb) comprises a reflector volume (Vrefl) of a reflector (201), an absorber volume (Vabs) of an absorber 202, and a fresh gas volume (Vfgas) of a fresh gas channel 203. The patient tubing volume (Vy) may here comprise an expiratory volume (Vexp) of the expiratory tube 104, and an inspiratory volume (Vinsp) of the inspiratory tube 103. The at least one breathing circuit pressure sensor comprises a reflector sensor 116 adjacent to the reflector 201 for providing a reflector pressure (Prefl), and a fresh gas sensor 113 adjacent to the fresh gas channel 203 for providing a fresh gas pressure (Pfgas). The at least one patient tubing pressure sensor comprises an expiratory sensor 115 adjacent to the expiration port 119 for providing an expiratory pressure (Pexp), and a inspiratory sensor 114 adjacent to the inspiration port 120 for providing a inspiratory pressure (Pinsp). The terms expiratory and inspiratory pressures are to be construed as adjectives for distinguishing the pressure values measured by the sensors 115, 114, respectively. I.e the expiratory sensor 115 measures and provides the expiratory pressure (Pexp), i.e the pressure at the sampling point of the expiratory sensor 115, to the pressure estimator unit 126 regardless if the breathing system 200 is in an expiratory phase or inspiratory phase, and likewise for the inspiratory sensor 114.

Applying the above principle for determining the volume weighted pressure (Pv), Pv=(Vb*Pb+Vy*Pp)/(Vb+Vy), to the system 300 the volume weighted pressure (Pv) during the inspiratory phase may be determined according to the relationship;

$$P_V = \frac{\frac{(V_{refl} + V_{abs}) \cdot (P_{refl} + P_{insp})}{2} + \frac{V_{fgas} \cdot (P_{fgas} + P_{insp})}{2} + \frac{V_{insp} \cdot (P_{insp} + P_{exp})}{2} + V_{exp} \cdot P_{exp}}{(V_{refl} + V_{abs} + V_{fgas} + V_{insp} + V_{exp})}$$

Thus, the sum of the volumes of each component multiplied with the mean pressure at the respective volumes is divided by the total volume. The above relationship may be adjusted depending on the introduction or removal of components in the breathing system 300.

Figure 4:
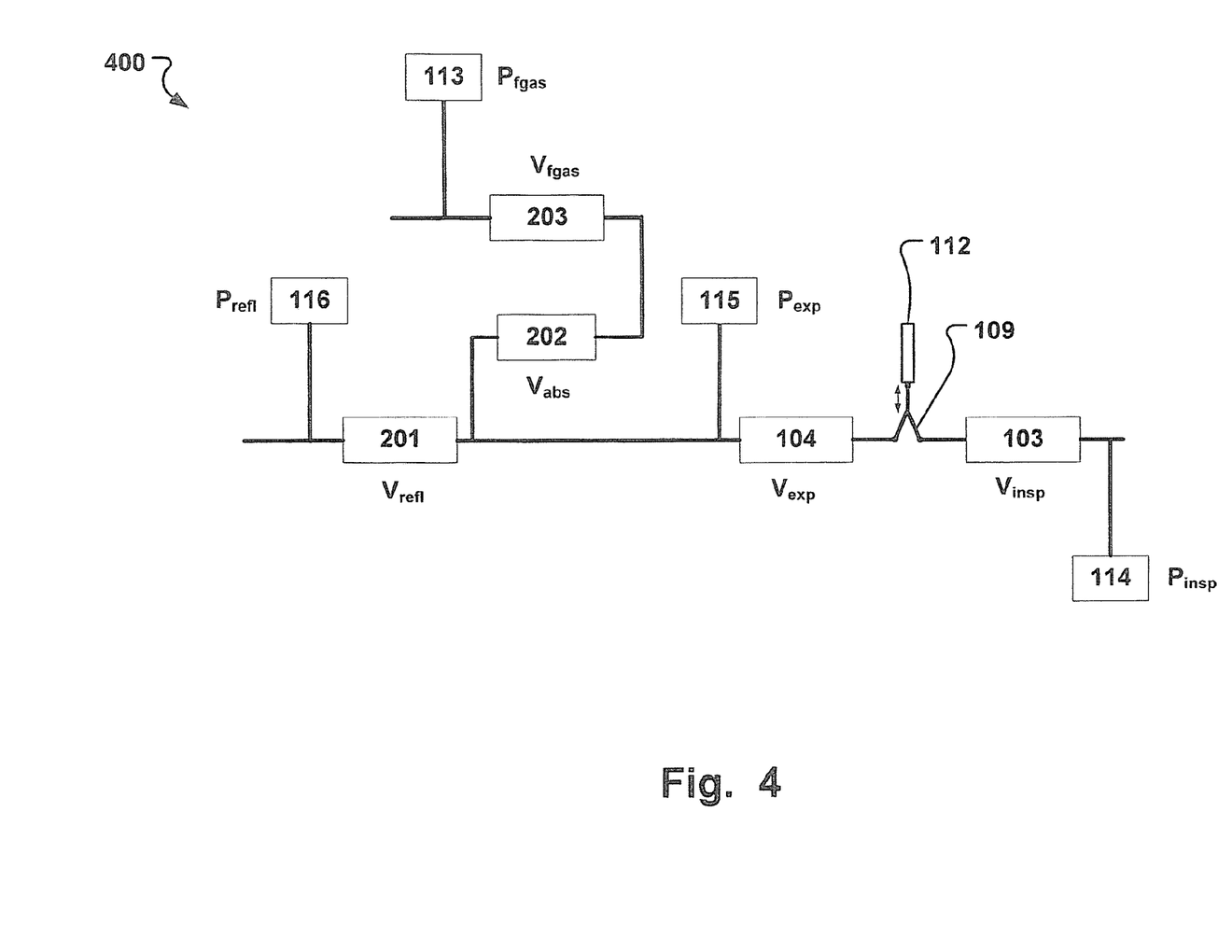
FIG. 4 is a schematic illustration of a breathing system for determining a volume weighted pressure according to an embodiment.

FIG. 4 shows schematic details of a breathing system 400 which is a simplified overview for illustrating the gas channel volumes (V) of the system 200 in FIG. 2 during the expiratory phase. During an expiratory phase of the system 200 the volume weighted pressure (Pv) is determined according to the relationship;

$$P_V = \frac{\frac{V_{refl} \cdot (P_{refl} + P_{exp})}{2} + \frac{(V_{fgas} + V_{abs}) \cdot (P_{fgas} + P_{exp})}{2} + \frac{V_{exp} \cdot (P_{insp} + P_{exp})}{2} + V_{insp} \cdot P_{insp}}{(V_{refl} + V_{abs} + V_{fgas} + V_{insp} + V_{exp})}$$

A linear pressure drop is assumed for all volumes in the systems 100-500. Alternatively, or additionally, a non-linear pressure drop may be compensated for.

Figures 5A, 5B:
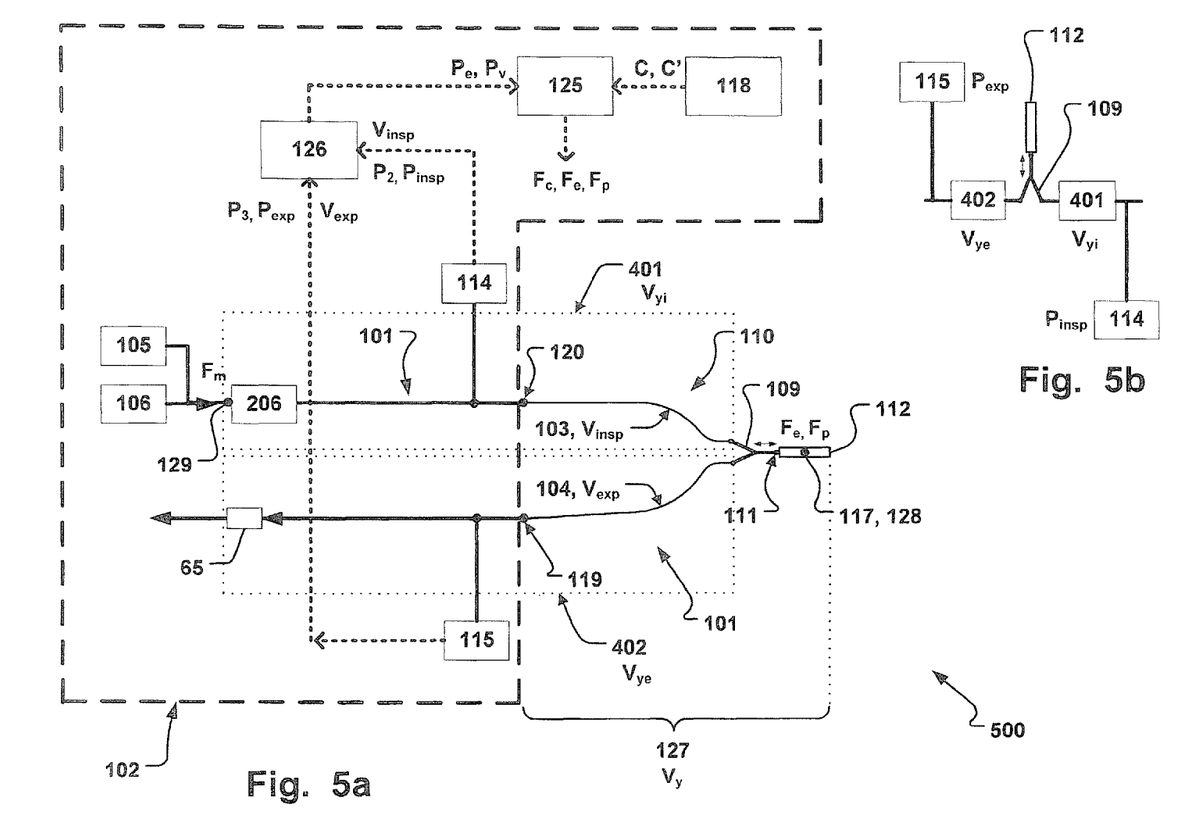
FIG. 5a is a schematic illustration of a breathing system according to an embodiment.
FIG. 5b is a schematic illustration of a breathing system for determining a volume weighted pressure according to an embodiment.

FIG. 5a shows a schematic illustration of a breathing system 500 according to an embodiment of the invention. The breathing system 500 may be used for ventilating a patient. The sub volumes (Vk) of the gas channel volume (V) in the breathing system 500 comprises a total inspiratory volume (Vyi) of an inspiratory line (401), and a total expiratory volume (Vye of an expiratory line (402). In comparison to FIG. 2, the total inspiratory volume (Vyi) comprises the inspiratory volume (Vinsp) of the inspiratory tube 103 and the inspiratory volume of the breathing circuit 102 in the gas channels 101 from the at least one gas source 105, 106, to the inspiration port 120, i.e. the inspiratory volume of the breathing circuit volume (Vb). Likewise, the total expiratory volume (Vye) includes the expiratory volume (Vexp) of the expiratory tube 104 and the expiratory volume of the breathing circuit 102 in the gas channels 101 from the expiration port 119 to the expiratory valve 65, i.e. the expiratory volume of the breathing circuit volume (Vb). The volume of the inspiratory and expiratory tube 103, 104, may be significantly larger than the volume in the breathing circuit 102. The pressure estimator unit 126 may be operative to determine the volume weighted pressure (Pv) according to a relationship between the total inspiratory volume (Vyi) and the total expiratory volume (Vye) and at least one pressure measured by the at least one pressure sensor, 114, 115.

During an inspiratory phase, an expiratory sensor 115 adjacent to the expiration port 119 provides an expiratory pressure (Pexp), which is a close estimate of the pressure at the y-piece 109 as there is no flow in the expiratory tube 119 that may cause a pressure drop. Simultaneously an inspiratory sensor 114 adjacent to the inspiration port 120 provides an inspiratory pressure (Pinsp). Likewise, during an expiratory phase, the inspiratory pressure (Pinsp) provided by the inspiratory sensor 114 is a close estimate of the pressure at the y-piece 109.

The volume weighted pressure (Pv) of the breathing system 500 may be regarded as a compliance weighted pressure (Pc) if the volume of the expiratory and inspiratory tube, 119, 120, are large in comparison to the volume of the breathing circuit 102, and if the expiratory and inspiratory tube 103, 104 are comprised of a flexible material that may cause changes in the volume.

FIG. 5b illustrates the gas channel volumes (V), i.e. the total inspiratory (Vyi) and expiratory volume (Vye) of the system 500 in FIG. 5a. During the inspiratory phase of the system 500 the volume weighted pressure (Pv) may be determined according to the relationship:

$$P_V = \frac{\frac{V_{yi} \cdot (P_{insp} + P_{exp})}{2} + V_{ye} \cdot P_{exp}}{(V_{yi} + V_{ye})}$$

and during an expiratory phase of the system 500 the volume weighted pressure (Pv) may be determined according to the relationship:

$$P_V = \frac{\frac{V_{ye} \cdot (P_{insp} + P_{exp})}{2} + V_{yi} \cdot P_{insp}}{(V_{yi} + V_{ye})}.$$

If the compliance of the inspiratory tube 103 equals the compliance of the expiratory tube 104, Pv may during inspiration be expressed as Pv=(Pinsp+3*Pexp)/4 and during expiration Pv=(3*Pinsp+Pexp)/4 This may be utilized if the compliance is estimated to be equal or if the compliance can not be measured separately for the inspiratory and expiratory tubes 103, 104.

Subsequently, the patient gas flow (Fp) at a patient interface 112 may be determined, according to the previous relationship Fp=Fm−C*dPv/dt, where Fm may be the total gas flow output from the at least one gas source 105-106 into the breathing circuit 102. The total gas flow output from the at least one gas source 105-106 may be determined by a flow meter 206 adjacent to the at least one gas source 105-106.

The compliance (C) of the system may be depending on the compression process. In this case the compliance (C) varies during a breath cycle of the patient. The compliance (C) of the system may hence be temperature dependent. The compliance estimator unit 118 may be operative to determine the compliance (C) based on a isotherm compliance (Ciso) and an adiabatic compliance (Cad) of the breathing system 100, 200, 500, and a time constant (τ) that describes the rate of transition from the adiabatic compliance (Cad) to the isotherm compliance (Ciso). The rate describes how fast thermal equilibrium is achieved in the breathing system 100, 200, 500. The difference (Ciso−Cadi) describes how much more compliant the system is to infinitely slow compressions compared to infinitely quick compressions.

Since the compliance (C) may vary during the breath, the estimate of the compressive gas flow (Fc) required to create a pressure rate of change (dP/dt) in the system may need to be compensated for the varying compliance. This may be done through the modified relationship Fc=Cfix*dP/dt+Ftherm, where Ftherm is an added calculated flow term and Cfix is a fixed compliance value determined by the compliance estimator unit 118, and where dP may correspond to dPe or dPv defined previously. The added flow term (Ftherm) represents an imaginary flow that is due to thermal effects in the compressed gas, and depends on the parameters {Ciso,Cadi,τ} and the pressure variation history of the compressed gas in the system 100, 200, 500.

One way of constructing the calculated flow term (Ftherm) is to consider an imaginary volume that is connected to the system via a imaginary flow constriction. The imaginary gas pressure (Ptherm) in the imaginary volume is calculated through the differential equation dPtherm/dt=(P−Ptherm)/τ. In analogy with the estimated compressive gas flow (Fc), the imaginary flow (Ftherm) into the imaginary volume is calculated from the relation Ftherm=Ctherm* dPtherm/dt, where Ctherm is the compliance of the imaginary volume.

The system 200 may have a low pass filter (not shown) for filtering of the signals from the pressure sensors 113-116 comprising the pressure values (P1, P2, P3, P4). A more accurate gas flow estimate (Fe) may be provided in case the signal from the pressure sensors 113-116 contains noise.

Figure 6:
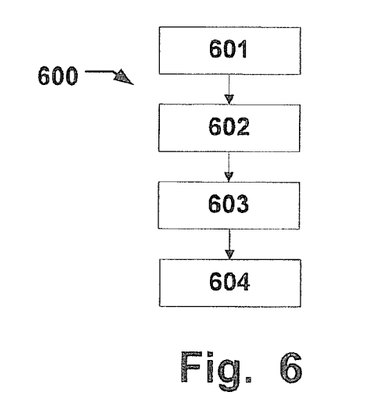
FIG. 6 is flow chart illustrating a method.

FIG. 6 is flow chart illustrating a method 600 of internally controlling a breathing system 100, 200, 500 having a gas channel having a gas channel volume (V) and a compliance (C). The method comprises determining 601 a gas flow estimate (Fe) at a flow estimate location in the gas channel, where the gas flow estimate (Fe) is based on a relationship between a monitored gas flow (Fm) in the gas channel and a compressible gas flow (Fc) which depends on the compliance (C) in the gas channel. The monitored gas flow (Fm) is determined at a monitoring location in the gas channel and the compressible gas flow (Fc) is a flow of gas in the gas channel between the flow estimate location and the monitoring location, and the flow estimate location is remote from the monitoring location.

The patient interface 112 or y-piece 109 may in the method be connected to a test lung. In another embodiment of the method a patient may be connected to the patient interface 112.

The system may have at least one pressure sensor in communication with the breathing system, and the method may further comprise measuring 602 at least one pressure at a pressure measurement location in the breathing system, determining 603 an estimated pressure (Pe) in the system from the at least one pressure, determining 604 the compressible gas flow (Fc) in the system based on a relationship between the compliance and a differential of the estimated pressure for providing the gas flow estimate (Fe).

The system may have a breathing circuit, and the gas flow estimate (Fe) may be a patient gas flow (Fp) in a patient interface connected to the breathing circuit. The patient gas flow (Fp) may be determined according to the relationship Fp=Fm−C*dPe/dt, wherein the differential is dPe/dt which is the time derivative of the estimated pressure (Pe), or the volume weighted pressure (Pv).

Figure 7:
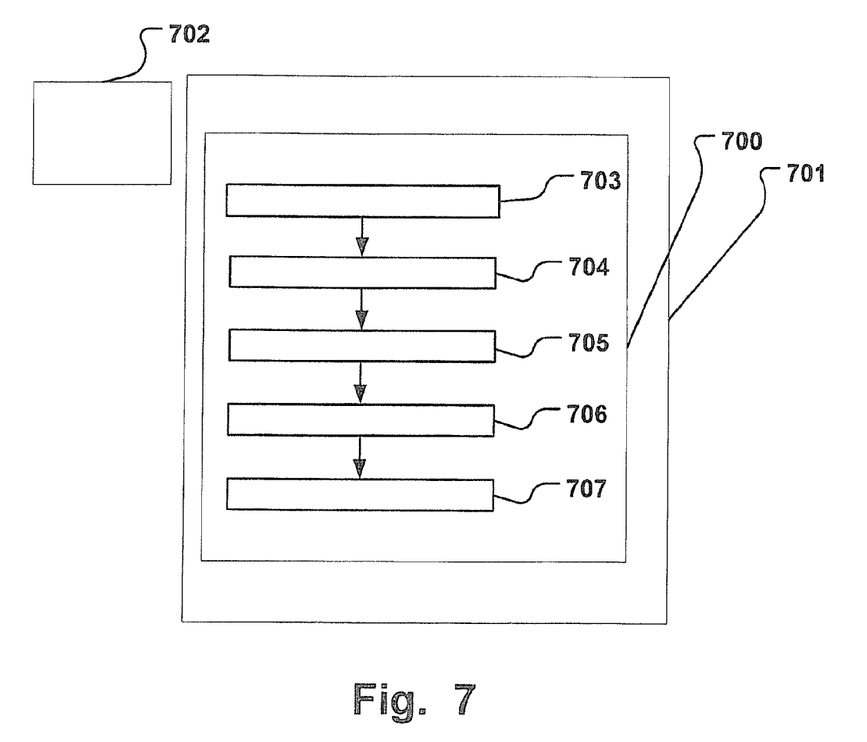
FIG. 7 is a schematic illustration of a computer program.

FIG. 7 is a schematic illustration of a computer program 700 that is stored on a computer readable medium 701, for processing by a computer 702. The computer 702 may be the flow calculation unit 125. The computer program 700 inlcudes code segments for measuring 703 at least one pressure at a pressure measurement location in a breathing system 100, 200, 500, having a compliance, determining 704 an estimated pressure (Pe) in the breathing system from the at least one pressure, determining 705 a compressible gas flow (Fc) in the breathing system based on a relationship between the compliance and a differential of the estimated pressure (Pe), determining 706 a gas flow estimate (Fe) in the breathing system based on a relationship between the compressible gas flow (Fc) and a monitored gas flow (Fm) in the breathing system. The gas flow estimate (Fe) may be determined at a flow estimate location, and the monitored gas flow (Fm) may be determined at a monitoring location in the gas channel, and the flow estimate location may be remote from the monitoring location, and/or the flow estimate location may be remote from the at least one pressure measurement location.

The system may have a breathing circuit, and the gas flow estimate may be a patient gas flow (Fp) in a patient interface connected to the breathing circuit. The computer program may comprise code segments for determining 707 the patient gas flow (Fp) according to the relationship Fp=Fm−C*dPe/dt, where the differential is dPe/dt which is the time derivative of the estimated pressure (Pe).

The present invention has been described above with reference to specific embodiments. However, other embodiments than the above described are equally possible within the scope of the invention. The delivery devices may in some embodiments for instance be a nebulizer for adding droplets of the substance to the gas stream. Different method steps than those described above, performing the method by hardware or software, may be provided within the scope of the invention. The different features and steps of the invention may be combined in other combinations than those described.

We claim as our invention:

1. A breathing system for ventilating a patient, comprising:
    a gas channel having a gas channel volume V and a compliance C;
    a monitoring location in said gas channel;
    a monitored gas flow Fm at said monitoring location which is either a measured flow at the monitoring location or a known flow from at least one gas source in communication with the gas channel;
    a flow estimate location in said gas channel at which a gas flow estimate Fe is determined, said flow estimate location being remote from said monitoring location;
    a plurality of pressure sensors measuring a respective plurality of pressures at different pressure measurement locations of said gas channel; and
    a computer comprising a program and operative to determine said gas flow estimate Fe at said flow estimate location and wherein said gas flow estimate is based on a relationship between said monitored gas flow Fm and a compressible gas flow Fc dependent on said compliance C, said compressible gas flow Fc being a flow of gas in said gas channel between said flow estimate location and said monitoring location, said computer also being operative to determine an estimated pressure Pe based on said plurality of measured pressures from said respective pressure sensors, and wherein said estimated pressure Pe is a volume weighted pressure Pv with respect to said gas channel volume V, and said computer also being operative to determine said compressible gas flow Fc based on a relationship between said compliance C and a differential of said estimated pressure Pe for determining said gas flow estimate Fe.

2. The breathing system according to claim 1 further comprising:
    said computer also being operative to determine said compliance C of said gas channel, and wherein said compliance C is a location specific compliance C' at an arbitrary location in said gas channel between said flow estimate location and said monitoring location.

3. The breathing system according to claim 1 wherein said flow estimate location is remote from at least one of said pressure measurement locations.

4. The breathing system according to claim 1 wherein said computer is operative to determine said compressible gas flow Fc according to the relationship Fc =C*dPe/dt wherein said differential is dPe/dt which is time derivative of said estimated pressure Pe.

5. The breathing system according to claim 1 further comprising:
    a breathing circuit; and
    a patient tubing connected to said breathing circuit, wherein said gas flow estimate Fe is a patient gas flow Fp in said patient tubing, and wherein said patient gas flow is determined according to the relationship Fp=Fm−C*dPe/dt wherein said differential is dPe/dt which is time derivative of said estimated pressure Pe.

6. The breathing system according to claim 5 wherein said gas channel volume V comprises a plurality of sub volumes Vk, and wherein said computer is operative to determine said volume weighted pressure Pv according to the relationship Pv=Σ(Vk*Pk)/ΣVk, where Pk is a measured pressure in each of said plurality of sub volumes respectively.

7. The breathing system according to claim 6 wherein said plurality of sub volumes comprises a breathing circuit volume $V_b$ of said breathing circuit and a patient tubing volume $V_y$ of said patient tubing, wherein said pressure sensors comprise:
    at least one breathing circuit pressure sensor adjacent to said breathing circuit volume $V_b$ for providing a breathing circuit pressure $P_b$; and
    at least one patient tubing pressure sensor for providing a patient tubing pressure $P_p$, wherein said computer is operative to determine said volume weighted pressure Pv according to the relationship $P_v=(V_b*P_b+V_y*P_p)/(V_b+V_y)$.

8. The breathing system according to claim 7 wherein said patient tubing comprises:
    y-piece tubing having an inspiratory tube and an expiratory tube; and
    a y-piece connectable to said breathing circuit via said y-piece tubing, said y-piece having a patient connection port, wherein said y-piece has a patient interface connected to said patient connection port, wherein said flow estimate location is a patient interface location in said patient interface, and wherein said patient gas flow Fp is determined at said patient interface location.

9. The breathing system according to claim 8 wherein at least one of said pressure measurement locations is positioned away from said patient interface location by at least a distance corresponding to a length of said y-piece tubing.

10. The breathing system according to claim 9 wherein said y-piece tubing is connected to said breathing circuit at expiration and inspiration ports of said breathing system, and wherein said at least one patient tubing pressure sensor is adjacent to at least one of an expiration port and an inspiration port.

11. The breathing system according to claim 10 wherein said computer is operative to determine said compliance C based on a breathing circuit compliance Cb and a y-piece compliance Cy when said patient connection port is plugged, wherein said y-piece compliance is the compliance of said y-piece tubing and said y-piece.

12. The breathing system according to claim 11 wherein said patient interface comprises:
    a proximal part disposed at said patient connection port and an opposite distal part, wherein said patient gas flow is determined at said distal part, wherein said computer is operative to determine said compliance C based on said breathing circuit compliance Cb and said y-piece compliance Cy when said patient interface is plugged, and wherein said y-piece compliance is the compliance of said y-piece tubing, said y-piece, and said patient interface.

13. The breathing system according to claim 10 wherein two of said gas sources are provided comprising a fresh gas source and a drive gas source, and further comprising:
two breathing circuit pressure sensors adjacent to each of said fresh gas source and said drive gas source; and
two patient tubing pressure sensors adjacent to each of said expiration and inspiration ports.

14. The breathing system according to claim 6 wherein said plurality of sub volumes comprises:
a total inspiratory volume Vyi of an inspiratory line in said breathing system; and
a total expiratory volume Vye of an expiratory line in said breathing system, wherein said computer is operative to determine said volume weighted pressure Pv according to a relationship between said total inspiratory volume and said total expiratory volume and at least one pressure measured by at least one of said pressure sensors.

15. The breathing system according to claim 14 wherein said pressure sensors comprise:
an expiratory pressure sensor adjacent to said total expiratory volume for providing an expiratory pressure Pexp; and
an inspiratory pressure sensor adjacent to said total expiratory volume for providing an inspiratory pressure Pinsp,
wherein said volume weighted pressure Pv is determined according to at least one of the following relationships, during an inspiratory phase of said system $$P_V = \frac{\frac{V_{yi} \cdot (P_{insp} + P_{exp})}{2} + V_{ye} \cdot P_{exp}}{(V_{yi} + V_{ye})},$$

during an expiratory phase of said system $$P_V = \frac{\frac{V_{ye} \cdot (P_{insp} + P_{exp})}{2} + V_{yi} \cdot P_{insp}}{(V_{yi} + V_{ye})}.$$

16. The breathing system according to claim 15 wherein said expiratory pressure sensor is adjacent to an expiration port, and wherein said inspiratory pressure sensor is adjacent to an inspiration port.

17. The breathing system according to claim 8 wherein said breathing circuit volume comprises
a reflector volume Vrefl of a reflector,
an absorber volume Vabs of an absorber, and
a fresh gas volume Vfgas of a fresh gas channel,
a volume of said patient tubing comprises
an expiratory volume Vexp of said expiratory tube, and
an inspiratory volume Vinsp of said inspiratory tube,
said pressure sensors comprise,
a reflector pressure sensor adjacent to said reflector for providing a reflector pressure Prefl,
a fresh gas pressure sensor adjacent to a fresh gas channel for providing a fresh gas pressure Pfgas,
an expiratory pressure sensor adjacent to said expiration port for providing an expiratory pressure Pexp, and
an inspiratory pressure sensor adjacent to said inspiration port for providing an inspiratory pressure Pinsp.

18. The breathing system according to claim 1 wherein volume weighted pressure Pv is determined according to at least one of the following relationships:
during an inspiratory phase of said system $$P_V = \frac{\frac{(V_{refl} + V_{abs}) \cdot (P_{refl} + P_{insp})}{2} + \frac{V_{fgas} \cdot (P_{fgas} + P_{insp})}{2} + \frac{V_{insp} \cdot (P_{insp} + P_{exp})}{2} + V_{exp} \cdot P_{exp}}{(V_{refl} + V_{abs} + V_{fgas} + V_{insp} + V_{exp})},$$

during an expiratory phase of said system $$P_V = \frac{\frac{V_{refl} \cdot (P_{refl} + P_{exp})}{2} + \frac{(V_{fgas} + V_{abs}) \cdot (P_{fgas} + P_{exp})}{2} + \frac{V_{exp} \cdot (P_{insp} + P_{exp})}{2} + V_{insp} \cdot P_{insp}}{(V_{refl} + V_{abs} + V_{fgas} + V_{insp} + V_{exp})}.$$

19. The breathing system according to claim 2 wherein said computer determines said compliance C based on an isotherm compliance Ciso and an adiabatic compliance Cad wherein a time constant τ describes a rate of transition from said adiabatic compliance to said isotherm compliance due to a temperature dependence in said system.

20. The breathing system according to claim 19 wherein said computer is operative to determine said gas flow estimate Fe according to the relationship Fe=Fm−C*dPe/dt−Ftherm (t), where Ftherm(t) is a thermal flow for correction of said temperature dependence at time t, wherein said thermal flow depends on said adiabatic compliance and said isotherm compliance, and wherein said differential is dPe/dt which is time derivative of said estimated pressure Pe.

21. The breathing system according to claim 1 comprising a low pass filter for filtering a signal comprising pressure values from at least one of said pressure sensors.

22. A method for ventilating a patient, comprising the steps of:
providing in a breathing system a gas channel having a gas channel volume V and a compliance C, a monitoring location in said gas channel, a monitored gas flow Fm at said monitoring location which is either a measured flow at the monitoring location or a known flow from at least one gas source in communication with the gas channel, a flow estimate location in said gas channel at which a gas flow estimate Fe is determined, said flow estimate location being remote from said monitoring location, a plurality of pressure sensors measuring a respective plurality of pressures at different pressure measurement locations of said gas channels, and a computer comprising a program; and
with said computer determining said gas flow estimate Fe at said flow estimate location and wherein said gas flow estimate is based on a relationship between said monitored gas flow Fm and a compressible gas flow Fc depended on said compliance C, said compressible gas flow Fc being a flow of gas in said gas channel between said flow estimate location and said monitoring location, determining an estimated pressure Pe based on said plurality of measured pressures from said respective pressure sensors, and wherein said estimated pressure Pe is a volume weighted pressure Pv with respect to said gas channel volume V, and with said computer also determining said compressible gas flow Fc based on a relationship between said compliance C and a differential of said estimated pressure Pe for determining said gas flow estimate Fe.

23. The method according to claim 22 wherein said breathing system includes a breathing circuit, and wherein said gas flow estimate Fe is a patient gas flow Fp in a patient interface connected to said breathing circuit, said patient gas flow being determined according to the relationship $Fp=Fm-C*dPe/dt$ wherein said differential is $dPe/dt$ which is time derivative of said estimated pressure Pe.

\* \* \* \* \*